United States Patent
Petyaev

(10) Patent No.: US 11,717,492 B2
(45) Date of Patent: Aug. 8, 2023

(54) METHODS FOR IMPROVING THE MICROBIOME AND ITS SYSTEMIC EFFECT

(71) Applicant: IP SCIENCE LIMITED, Cambridge (GB)

(72) Inventor: Ivan Petyaev, Cambridge (GB)

(73) Assignee: IP SCIENCE LIMITED, Cambridge (GB)

(*) Notice: Subject to any disclaimer, the term of this patent is extended or adjusted under 35 U.S.C. 154(b) by 275 days.

(21) Appl. No.: 17/050,127

(22) PCT Filed: Apr. 26, 2019

(86) PCT No.: PCT/GB2019/051169
§ 371 (c)(1),
(2) Date: Oct. 23, 2020

(87) PCT Pub. No.: WO2019/207316
PCT Pub. Date: Oct. 31, 2019

(65) Prior Publication Data
US 2021/0077418 A1    Mar. 18, 2021

(30) Foreign Application Priority Data
Apr. 27, 2018    (GB) .................................. 1806941

(51) Int. Cl.
A61K 31/01    (2006.01)
A61K 31/015    (2006.01)
A23L 33/105    (2016.01)
A23L 33/135    (2016.01)
A61K 35/745    (2015.01)
A61K 35/747    (2015.01)

(52) U.S. Cl.
CPC .......... *A61K 31/015* (2013.01); *A23L 33/105* (2016.08); *A23L 33/135* (2016.08); *A61K 35/745* (2013.01); *A61K 35/747* (2013.01)

(58) Field of Classification Search
CPC .................................................... A61K 31/01
See application file for complete search history.

(56) References Cited

FOREIGN PATENT DOCUMENTS

| | | |
|---|---|---|
| CN | 102145016 | 8/2011 |
| EP | 1618800 | 1/2006 |
| WO | 2017/046711 | 3/2017 |
| WO | 2017/144062 | 8/2017 |

OTHER PUBLICATIONS

English machine translation of He et al., CN 100443115 C, 2008.*
Costes et al., "Age-associated alteration of muscle oxygenation measured by near infrared spectroscopy during exercise", Arch Physiol Biochem, 1999, vol. 107, No. 2, pp. 159-167.
Marseglia et al., "Oxidative Stress in Obesity: A Critical Component in Human Diseases", Int. J. Mol. Sci., 2015, vol. 16, pp. 378-400.

(Continued)

*Primary Examiner* — Rosanne Kosson
(74) *Attorney, Agent, or Firm* — Wenderoth, Lind & Ponack, LLP

(57) ABSTRACT

We describe that carotenoids provide a prebiotic effect and can be used to improve the health of the gut microbiome.

5 Claims, 2 Drawing Sheets

Figure 1:
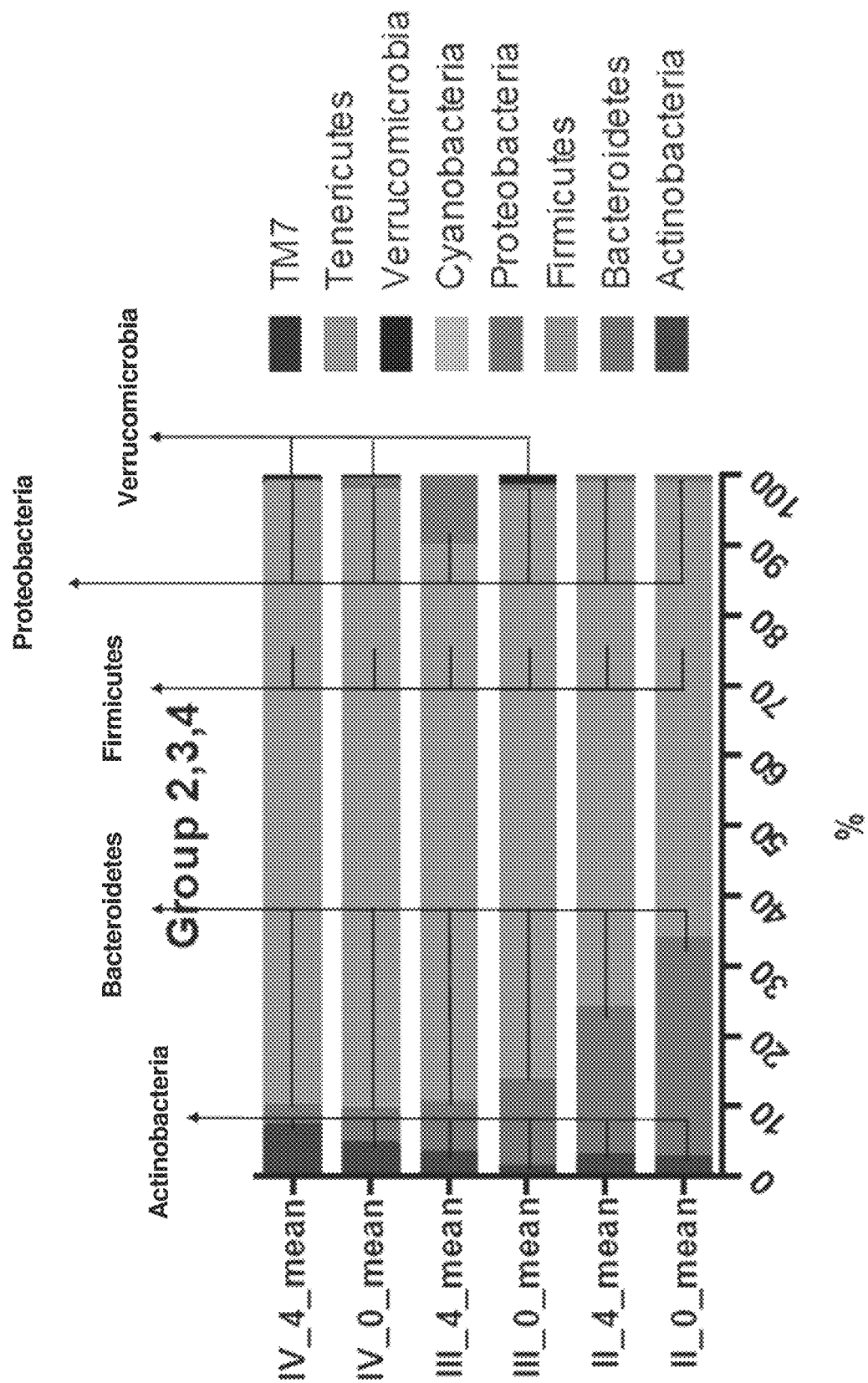

Specification includes a Sequence Listing.

(56) References Cited

OTHER PUBLICATIONS

Ovreas et al., "Distribution of Bacterioplankton in Meromictic Lake Saelenvannet, as Determined by Denaturing Gradient Gel Electrophoresis of PCR-Amplified Gene Fragments Coding for 16S rRNA", Applied and Environmental Microbiology, 1997, vol. 63, No. 9, pp. 3367-3373.

Kristensen et al., "Gut microbiota in children hospitalized with oedematous and non-oedematous severe acute malnutrition in Uganda", PLoS Negl Trop Dis, 2016, vol. 10, No. 1, e0004369.

Edgar, R. C., "UPARSE: highly accurate OTU sequences from microbial amplicon reads", Nature Methods, 2013, vol. 10, No. 10, pp. 996-998.

Caporaso et al., "QIIME allows analysis of high-throughput community sequencing data", Nature Methods, 2010, vol. 7, No. 5, pp. 335-336.

McDonald et al., "An improved Greengenes taxonomy with explicit ranks for ecological and evolutionary analyses of bacteria and archaea", The ISME Journal, 2012, vol. 6, pp. 610-618.

Petyaev et al., "Superoxide dismutase activity of antibodies purified from the human arteries and atherosclerotic lesions", 1998, Biochem. Soc. Trans, vol. 26, S43045.

Petyaev et al., "Clinical Study: Whey Protein Lycosome Formulation Improves Vascular Functions and Plasma Lipids with Reduction of Markers of Inflammation and Oxidative Stress in Prehypertension", The Scientific World Journal, 2012, Article ID 269476, 7 pages.

Servin, A. L., Antagonistic activities of lactobacilli and bifidobacteria against microbial pathogens, FEMS Microbiol Rev., 2004, vol. 28, No. 4, pp. 405-440.

O'Callaghan et al., "Bifidobacteria and Their Role as Members of the Human Gut Microbiota", Front Microbiol, 2016, vol. 7, Article 925.

Arboleya et al., "Gut Bifidobacteria Populations in Human Health and Aging", Front Microbiol, 2016, vol. 7, Article 1204.

Singh et al., "A novel cobiotic-based preventive approach against high-fat diet-induced adiposity, nonalcoholic fatty liver and gut derangement in mice", International Journal of Obesity, 2016, vol. 40, No. 3, pp. 487-496.

Dias et al., "Effects of lycopene, synbiotic and their association on early biomarkers of rat colon carcinogenesis", Food and Chemic Toxicology, 2010, vol. 48, No. 3, pp. 772-780.

Jung et al., "Butyrate modulates bacterial adherence on LS174T human colorectal cells by stimulating mucin secretion and MAPK signaling pathway", Nutrition Research and Practice, 2015, vol. 9, No. 4, pp. 343-349.

International Search Report dated Jul. 25, 2019 in corresponding International (PCT) Application No. PCT/GB2019/051169.

\* cited by examiner

METHODS FOR IMPROVING THE MICROBIOME AND ITS SYSTEMIC EFFECT

Significant interest has evolved on the gut microbiota, i.e. the entire population of microorganisms that colonizes a particular location, in recent years. The gut microbiota have been associated with a large array of human diseases ranging from luminal diseases such as inflammatory bowel diseases (IBD) and irritable bowel syndrome (IBS), allergies, metabolic diseases such obesity and diabetes, to neurodevelopmental illnesses. There is mounting evidence that the gut microbiota have a significant role in maintaining the gut and human health as a whole.

Prebiotics are non-microbial substances that can exert beneficial effect on the human body by helping the body's natural gut microflora to grow and/or by increasing their metabolic activity. The prebiotic concept was first proposed by Gibson and Roberfroid in 1995. The key aspects of a prebiotic are that it is not digestible by the host and that it leads to health benefits for the individual through a positive influence on native beneficial microbes. The administration or use of prebiotics or probiotics is intended to influence the gut environment, i.e. the microbiota, which is dominated by trillions of commensal microbes, for the benefit of human health. Prebiotics are dietary substances (mostly consisting of non-starch polysaccharides and oligosaccharides). Most prebiotics are used as food ingredients, for example in biscuits, cereals, chocolate, spreads, and dairy products. Commonly known prebiotics are: oligofructose, inulin, galacto-oligosaccharides, lactulose and breast milk oligosaccharides (World Gastroenterology Organisation Global Guidelines, Probiotics and prebiotics, 2017).

Prebiotics are often used in combination with probiotic microorganisms. Probiotics are live microbes that can be formulated into many different types of products, including foods, drugs, and dietary supplements. Species of *Lactobacillus* and *Bifidobacterium* are most commonly used as probiotics, but the yeast *Saccharomyces cerevisiae* and some *E. coli* and *Bacillus* species are also used as probiotics. Lactic acid bacteria (LAB), including species of *Lactobacillus*, which have been used for preservation of food by fermentation for thousands of years, can serve a dual function by acting as agents of food fermentation and, in addition, potentially imparting health benefits.

Prebiotics and probiotics have been shown to have a number of health benefits. Any composition that combines a probiotic and prebiotic is termed a symbiotic.

Carotenoids are the essential micronutrients, which cannot be synthesized by humans and must be obtained from food. Lycopene, the red pigment of tomatoes, watermelon and some other fruits is one major carotenoid. The current consensus on the broad beneficial effects of lycopene on health is that its powerful antioxidant properties can protect lipoproteins and other lipid structures from their oxidative damage, which typically occurs in a number of pathological conditions.

Although various prebiotic compositions are known in the art, there remains a need for effective prebiotic compositions which support the growth of health-beneficial bacteria. The present invention is aimed at addressing this need.

SUMMARY

There is emerging evidence that dysbiosis of the gut microbiome on the phylum level can alter representation of bacterial genes and their metabolic pathway, which in turn may contribute to the development of pathogenesis of a number of conditions, including obesity. An increase in *Bacteroides* has been implicated in development of obesity. In our study, we observed that continued intervention with carotenoids resulted in significant decrease in the abundance of Bacteroidetes. Moreover, we observed an increase in Actinobacteria, in particular in Bifidobacteria. Bifidobacteria are believed to exert positive health benefits on their host.

We have thus surprisingly found that carotenoids can provide a prebiotic effect on the gut microbiome. Accordingly, we provide methods for increasing the population of health-beneficial bacteria in the gut, methods for prophylactic and therapeutic treatment of the gut microbiome, compositions for therapeutic treatment of the gut microbiome as well as carotenoids for use as a prebiotic with systemic health beneficial effect to other organs in the body.

FIGURES

The invention is further illustrated in the following non-limiting figures.

FIG. 1. Changes in the gut microbiome after supplementation with 7 mg and two 30 mg lycopene formulations for one month:

2nd group—7 mg lycopene in cocoa butter.
3rd group—30 mg lycopene in cocoa butter.
4th group—30 mg lycopene sunflower oil.

An increase of Actinobacteria and reduction of Bacteroidetes was detected across the groups, with a proportional increase in relative abundance of Firmicutes for groups 2 and 4.

Figure 2:
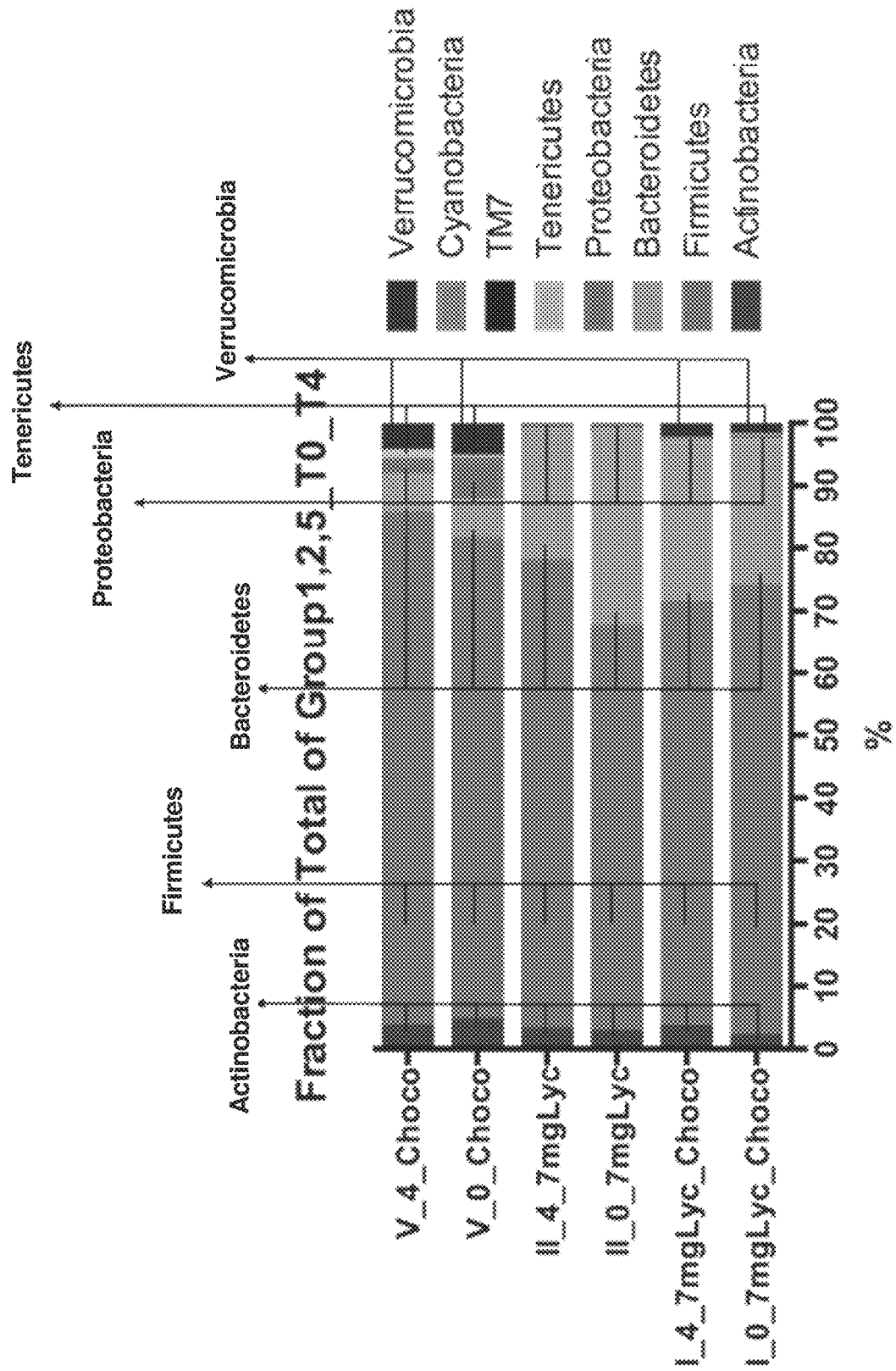

FIG. 2. Changes in the gut microbiome after continuous ingestion of dark chocolate, its formulation with 7 mg lycopene and control lycopene capsules for one month.

1st group—10 g dark chocolate with 7 mg lycopene.
2nd group—7 mg lycopene in cocoa butter, control in a capsule form.
5th group—10 g of dark chocolate control.

DETAILED DESCRIPTION

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

The study described herein reveals the beneficial effect of lycopene on the gut microbiota of humans. Surprisingly, we found that administration of lycopene resulted in a significant prebiotic effect. The positive changes in the gut microbiota profile were accompanied by systemic improvement of different parameters in the body of the participants. Results of this clinical study are presented in the examples.

Thus, in one aspect, we provide a use of a carotenoid compound in promoting growth and/or increasing the abundance of an Actinobacterium, for example *Bifidobacterium*, in the gastro-intestinal tract of a subject.

In another aspect, we provide a use of a carotenoid compound to make medical or functional food, functional beverage, nutraceutical or pharmaceutical products for promoting growth and/or increasing the abundance of an Actinobacterium, for example *Bifidobacterium*, in the gastro-intestinal tract of a subject.

In another aspect, we provide a method for promoting growth and/or increasing the abundance of an Actinobacterium, for example *Bifidobacterium*, in the gastro-intestinal tract of a subject, comprising administration of a carotenoid.

Thus, in one aspect, we provide a use of a carotenoid compound in decreasing growth and/or decreasing the abundance of a member of the phyla Bacteroidetes, in the gastro-intestinal tract of a subject.

In another aspect, we provide a use of a carotenoid compound to make medical or functional food, functional beverage, nutraceutical or pharmaceutical products for decreasing growth and/or decreasing the abundance of a member of the phyla Bacteroidetes in the gastro-intestinal tract of a subject.

In another aspect, we provide a method for decreasing growth and/or decreasing the abundance of a member of the phyla Bacteroidetes, in the gastro-intestinal tract of a subject, comprising administration of a carotenoid.

In another aspect, we provide a method for the prophylaxis or treatment of a gastro-intestinal condition in a subject, comprising administration of a carotenoid.

In another aspect, we provide a method for the prophylaxis or treatment of a condition which can be dependent on or associated with the status of the gastro-intestinal health in a subject comprising administration of a carotenoid. In one embodiment, said condition is a result of dysbiosis, that is an imbalanced microbiome.

In another aspect, we provide a method for stimulating beneficial *Bifidobacterium* microflora in subject.

In another aspect, we provide a composition comprising a carotenoid and one or more probiotic bacteria.

In another aspect, we provide a composition comprising a carotenoid and optionally one or more probiotic bacteria for use in the treatment of dysbiosis, of a gastrointestinal disease and/or for promoting growth or increasing the abundance of an Actinobacterium, for example *Bifidobacterium*, in the gastro-intestinal tract of a subject.

In another aspect, we provide a composition comprising a carotenoid and optionally one or more probiotic bacteria for use in the treatment of a disease which can be dependent on or associated with the status of the gastrointestinal health.

The methods and uses provided herein give a systemic health beneficial effect.

Carotenoid compounds are tetraterpenoids which contain long polyene chains. Carotenoid compounds include xanthophylls such as lutein and zeaxanthin, and carotenes, such as beta-carotene, alpha-carotene, zeto-carotene, and lycopene compounds.

In one embodiment of the various aspects set out herein, the carotenoid is a xanthophyll. In one embodiment, the xanthophyll is selected from the group consisting of α-cryptoxantin, β-cryptoxantin, adonirubin, adonixanthin, alloxanthin, amarouciaxanthin A, antheraxanthin, astaxanthin, auroxanthin, caloxanthin, cantaxanthin, capsanthin, capsanthin-5-6-epoxide, capsorubin, crocoxanthin, diadinoxanthin, diatoxanthin, echinenone, fucoxanthin, fucoxanthinol, iso-fucoxanthin, iso-fucoxanthinol, lutein, luteoxanthin, mutatoxanthin, neoxanthin, nostoxanthin, violaxanthin, zeaxanthin and combinations thereof.

In one embodiment, the carotenoid is a carotene. In another embodiment, the carotene is selected from the group consisting of α-carotene, β-carotene, γ-carotene, δ-carotene, ε-carotene, ζ-carotene, lycopene, neurosporene, phytoene, phytofluene and combinations thereof.

In one embodiment, the carotenes and xantophylles described above refer to the all-trans forms thereof. In another embodiment, the xantophylles and carotenes for use in the aspects of the present invention include derivatives containing one or more cis double bond.

In one embodiment, the carotenoid compound is a lycopene compound. Lycopene compounds may include lycopene, 1-HO-3',4'-didehydrolycopene, 3,1'-(HO) 2-gamma-carotene, 1,1'-(HO) 2-3,4,3',4'-tetradehydrolycopene, 1,1'-(HO) 2-3,4-didehydrolycopene.

In some embodiments, the carotenoid compound is a lycopene compound such as lycopene. Lycopene is an open-chain unsaturated C40 carotenoid of structure I (Chemical Abstracts Service Registry Number 502-65-8, $C_{40}H_{56}$).

Structure I

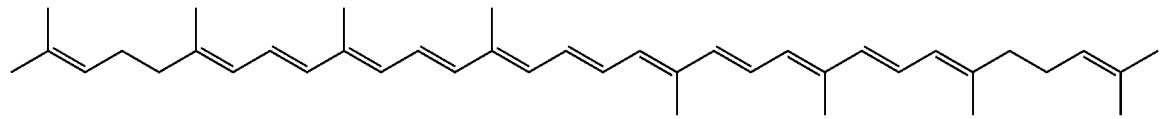

Lycopene occurs naturally in plants such as tomatoes, guava rosehip, watermelon and pink grapefruit and any such sources of lycopene may be, for instance, employed.

Lycopene for use as described herein may comprise one or more different isomers. For example, lycopene may include cis-lycopene isomers, trans-lycopene isomers and mixtures of the cis- and trans-isomers. Lycopene may comprise at least 10%, at least 20%, at least 30%, at least 40%, at least 50%, at least 60%, at least 70%, at least 80%, at least 90%, or at least 95% (Z)-isomers, (all-E)-isomers, or cis-isomers, such as 5-cis- or 9-cis- or 13-cis-isomers, which have improved bioavailability relative to trans isomers. Trans isomers may isomerise into cis forms in vivo, or during storage and processing.

Carotenoid compounds, such as lycopene, may be natural i.e. obtained from a natural source, for example, extracted from a carotenoid-rich fruit, vegetable or other plant, such as a tomato or melon, or from fungi, algae or bacteria. In one instance, the carotenoid compound may be, or comprise, oleoresin, particularly tomato oleoresin.

A range of methods for extracting, concentrating and/or purifying carotenoids from plants are known in the art. For example, solvent extraction using ethanol, DMSO, ethyl acetate, hexane, acetone, soya or other vegetable oil, or non-vegetable oils may be employed.

Carotenoid compounds, such as lycopene, for use as described herein may be synthetic i.e. produced by artificial means, for example, by chemical synthesis. A range of methods for chemical synthesis of lycopene and other carotenoids are known in the art. For example, a three-stage chemical synthesis based on the standard Wittig olefination reaction scheme for carotenoid synthesis may be employed, in which an organic solution of Ci5 phosphonium methanesulfonate in dichloromethane (DCM) and an organic solution of Ci0 dialdehyde in toluene are produced, and the two organic solutions are gradually combined with sodium methoxide solution and undergo a condensation reaction to form crude lycopene. The crude lycopene may then be purified using routine techniques, for example by adding glacial acetic acid and deionized water to the mixture, stirring vigorously, allowing the aqueous and organic phases to separate, and extracting the organic phase containing DCM and crude lycopene with water. Methanol is added to the organic phase and the DCM removed via distillation under reduced pressure. The crude methanolic lycopene solution is then be heated and cooled to crystalline slurry that is filtered and washed with methanol. The lycopene crystals may then be recrystalized and dried under heated nitrogen. Synthetic carotenoids, such as lycopene, are also available from commercial suppliers (e.g. BASF Corp, NJ USA).

Synthetic carotenoid compounds, such as lycopene, may comprise an increased proportion of cis isomers relative to natural carotenoid compounds. For example, synthetic lycopene may be up to 25% 5-cis, 1% 9-cis, 1% 13-cis, and 3% other cis isomers, whilst lycopene produced by tomatoes may be 3-5% 5-cis, 0-1% 9-cis, 1% 13-cis, and <1% other cis isomers. Since cis-lycopene has increased bioavailability relative to trans-lycopene, synthetic lycopene is preferred in some embodiments.

Derivatives of carotenoids as described above may be produced by chemical synthesis analogous to the synthesis described above or by chemical modification of natural carotenoids extracted from plant material. In one embodiment of the various aspects set out herein, the *Bifidobacterium* is selected from one of the following: *Bifidobacterium adolescentis, Bifidobacterium catenulatum, Bifidobacterium pseudocatenulatum, Bifidobacterium longum, Bifidobacterium angulatum, Bifidobacterium kashiwanohense, Bifidobacterium* dentum and *Bifidobacterium* stercoris.

In one embodiment, the subject has moderate obesity with a $30<BMI<35$ kg/m$^2$.

In one embodiment, the gastro-intestinal condition is selected from the group consisting of inflammatory bowel syndrome, constipation, diarrhoea, colitis, Crohn's disease, colon cancer, functional bowel disorder, irritable bowel syndrome. A condition dependent on or associated with gut health can be selected from metabolic syndrome, obesity, cardio- and cerebrovascular disease, neurodegenerative, mental and skin pathologies The amount of the carotenoid compound that is effective/active in the treatment of a particular disorder or condition will depend on the nature of the disorder or condition, and can be determined by standard clinical techniques. In addition, in vitro or in vivo assays can optionally be employed to help identify optimal dosage ranges. The precise dose to be employed in the compositions will also depend on the route of administration, and the seriousness of the disease or disorder, and should be decided according to the judgment of the practitioner and each patient's circumstances. Factors like age, body weight, sex, diet, time of administration, rate of excretion, condition of the host, drug combinations, reaction sensitivities and severity of the disease shall be taken into account. As used herein, the term "effective amount" means an amount of the carotenoid compound, that when administered to a subject, is effective to achieve the desired therapeutic or prophylactic effect under the conditions of administration. A subject as used herein is an animal, for example a mammal, for example a human, dog, cat, or horse or a non-mammalian species such as a bird or fish.

Administration may be together with one or more probiotic bacteria.

In another aspect, we provide a composition comprising a carotenoid and one or more probiotic bacteria. In another aspect, we provide a composition comprising a carotenoid and optionally one or more probiotic bacteria for use in the treatment of a gastrointestinal disease and/or for promoting growth or increasing the abundance of a *Bifidobacterium* in the gastro-intestinal tract of a subject.

Typically, the amount is at least about 0.0001% of the carotenoid compound by weight of the composition. When intended for oral administration, this amount can be varied to range from about 0.0001% to about 80% by weight of the composition. Preferred oral compositions can comprise from about 0.0004% to about 50% of the active of the present invention by weight of the composition.

Some compositions of the present invention are prepared so that a parenteral dosage unit contains from about 0.0001% to about 2% by weight of the carotenoid compound.

For administration by injection, the composition can comprise from about typically about 0.1 mg/kg to about 250 mg/kg of the animal's body weight, preferably, between about 0.1 mg/kg and about 20 mg/kg of the animal's body weight, and more preferably about 1 mg/kg to about 10 mg/kg of the animal's body weight. In one embodiment, the composition is administered at a dose of about 1 to 30 mg/kg, e.g., about 5 to 25 mg/kg, about 10 to 20 mg/kg, about 1 to 5 mg/kg, or about 3 mg/kg. The dosing schedule can vary from e.g., once a week to once every 2, 3, or 4 weeks.

For oral administration, the amount of carotenoid, for example lycopene, is 1-60 mg per day, for example about 5, 7, 10, 20, 30, 40 mg per day. Administration may be for at least 4 weeks.

The composition can be a pharmaceutical composition of a food supplement composition.

In one embodiment, the carotenoid compound is provided as part of a composition which includes an acceptable carrier.

The composition can be administered by any convenient route, including but not limited to oral, topical, parenteral, sublingual, rectal, vaginal, ocular, intranasal, pulmonary, intradermal, intrasynovial, epidural, intravitrial, intramuscular, intraperitoneal, intravenous, subcutaneous, intracerebral, transdermal, transmucosal, by inhalation, or topical, particularly to the ears, nose, eyes, or skin or by inhalation. In one embodiment, administration is oral.

Parenteral administration includes, for example, intravenous, intramuscular, intraarterial, intraperitoneal, intrasynovial, epidural, intranasal, rectal, intravesical, intradermal, topical or subcutaneous administration. Preferably, the compositions are administered parenterally.

The acceptable carrier or vehicle can be particulate, so that the compositions are, for example, in tablet or powder form. The term "carrier" refers to a diluent, adjuvant or excipient, with which a carotenoid compound is administered. Such pharmaceutical carriers can be liquids, such as water and oils, including those of petroleum, animal, vegetable or synthetic origin, such as peanut oil, soybean oil, mineral oil, sesame oil and the like. The carriers can be saline, gum acacia, gelatin, starch paste, talc, keratin, colloidal silica, urea, and the like. In addition, auxiliary, stabilizing, thickening, lubricating and colouring agents can be used. Water is a one carrier. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The compositions, if desired, can also contain minor amounts of wetting or emulsifying agents, or pH buffering agents.

The composition can be in the form of a liquid, e.g., a solution, emulsion or suspension. The liquid can be useful for delivery by injection, infusion (e.g., IV infusion) or sub-cutaneously.

When intended for oral administration, the composition can be in solid or liquid form, e. g. an elixir, syrup, solution, emulsion or suspension, where semi-solid, semi-liquid, suspension and gel forms are included within the forms considered herein as either solid or liquid. The liquid can be useful for oral administration or for delivery by injection. When intended for oral administration, a composition can comprise one or more of a sweetening agent, preservatives, dye/colorant and flavour enhancer. In a composition for administration by injection, one or more of a surfactant, preservative, wetting agent, dispersing agent, suspending agent, buffer, stabilizer and isotonic agent can also be included.

As a solid composition for oral administration, the composition can be formulated into a powder, granule, compressed tablet, pill, capsule, chewing gum, wafer or the like form. Such a solid composition typically contains one or more inert diluents. In addition, one or more of the following can be present: binders such as carboxymethylcellulose, ethyl cellulose, microcrystalline cellulose, or gelatin; excipients such as starch, lactose or dextrins, disintegrating agents such as alginic acid, sodium alginate, corn starch and the like; lubricants such as magnesium stearate; glidants such as colloidal silicon dioxide; sweetening agents such as sucrose or saccharin; a flavoring agent such as peppermint, methyl salicylate or orange flavoring; and a coloring agent. When the composition is in the form of a capsule (e. g. a gelatin capsule), it can contain, in addition to materials of the above type, a liquid carrier such as polyethylene glycol, cyclodextrin or a fatty oil.

Compositions may be formulated to release the carotenoid compound substantially immediately upon administration or at any predetermined time or time period after administration. In one example, controlled release is obtained by appropriate selection of various formulation parameters and ingredients, including, e.g., various types of controlled release compositions and coatings. Thus, the carotenoid compound is formulated with appropriate excipients into a pharmaceutical composition that, upon administration, releases the therapeutic in a controlled manner. Examples include single or multiple unit tablet or capsule compositions, oil solutions, suspensions, emulsions, microcapsules, microspheres, molecular complexes, nanoparticles, patches, and liposomes.

Compositions can take the form of one or more dosage units.

In one embodiment, administration of the carotenoid compound is part of a combination therapy. The carotenoid compound may be co-administered with the other therapy or given at another time.

In another embodiment, the subject may have previously received another therapy.

In another aspect, we provide a composition comprising a carotenoid and one or more probiotic bacteria. The composition may be a pharmaceutical composition according to the embodiments above. In one embodiment, the carotenoid is lycopene. In one embodiment, the one or more probiotic bacteria are selected from the group consisting of: *Lactobacillus plantarum, Lactobacillus acidophilus, Lactobacillus paracasei, Leuconostoc mesenteroides, Lactobacillus bulgaricus, Lactobacillus casei, Lactobacillus salivarius, Acidophilus, Acidophilus Bifidus, Acidophilus Lactobacillus, L. Acidophilus, L. Amylovorus, L. Brevis, L. Casei Immunitas, L. Crispatus, L. Delbrueckii, L. Fermentum, L. Gallinarum, L. Helveticus, L. Johnsonii, L. Johnsonii LC-1, L. Lactis, L. Plantarum, L. Reuteri, L. Rhamnosus, L. Salivarius, L. Sporogenes, Lacto Bacillus*, Lactobacille, Lactobacilli, Lactobacilli *Bulgaricus*, Lactobacilli *Plantarum*, Lactobacilli *Rhamnosus*, Lactobacilli *Salivarium, Lactobacillus acidophilus, Lactobacillus amylovorus, Lactobacillus brevis, Lactobacillus bulgaricus, Lactobacillus casei, Lactobacillus casei sp. rhamnosus, Lactobacillus crispatus, Lactobacillus delbrueckii, Lactobacillus delbrueckii ssp. bulgaricus, Lactobacillus fermentum, Lactobacillus gallinarum, Lactobacillus* Gasseri, *Lactobacillus GG, Lactobacillus Helveticus, Lactobacillus johnsonii, Lactobacillus Lactis, Lactobacillus reuteri, Lactobacillus Rhamnosus GG, Lactobacillus rhamnosus, Lactobacillus sakei, Lactobacillus sporogenes*, Lactobacilo, Lactospores, LC-1, Probiotics, Probiotiques, *Pediococcus pentosaceus, Streptococcus thermophilus, Bacillus subtilis, Bacillus coagulans, Enteroccous faecium, Bifidobacterium bifidum, Bifidobacterium lactis, Bifidobacterium longum*, and *Bifidobacterium infantis, Bifidobacterium breve, Bifidobacterium animalis* or *Bifidobacterium longum.*

In another aspect, we provide a kit comprising a carotenoid and one or more probiotic bacteria. In another aspect, we provide a kit comprising a carotenoid and optionally one or more probiotic bacteria, for use in the treatment of a gastrointestinal disease or a disease associated with the gastrointestinal tract and/or for promoting growth or increasing the abundance of an Actinobacterium, for example *Bifidobacterium*, in the gastro-intestinal tract of a subject.

Unless otherwise defined herein, scientific and technical terms used in connection with the present disclosure shall have the meanings that are commonly understood by those of ordinary skill in the art. While the foregoing disclosure provides a general description of the subject matter encompassed within the scope of the present invention, including methods, as well as the best mode thereof, of making and using this invention, the following examples are provided to further enable those skilled in the art to practice this invention and to provide a complete written description thereof. However, those skilled in the art will appreciate that the specifics of these examples should not be read as limiting on the invention, the scope of which should be apprehended from the claims and equivalents thereof appended to this disclosure. Various further aspects and embodiments of the present invention will be apparent to those skilled in the art in view of the present disclosure.

All documents mentioned in this specification are incorporated herein by reference in their entirety.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein. Unless context dictates otherwise, the descriptions and definitions of the features set out above are not limited to any particular aspect or embodiment of the invention and apply equally to all aspects and embodiments which are described.

The invention is further described in the non-limiting examples.

Examples

Materials and Methods

Study Design. The total number of volunteers recruited to take part in the study was 30 (15 male and 15 female subjects) Caucasians 40-67 years old. They were randomised and divided into five groups of equal size. Group I received a daily dose of 10 g dark chocolate with 7 mg lycopene by a proprietary protocol guaranteeing its maximum embedment into the lipid part of the chocolate, L-Tug, and on another optimal lycopene coating of chocolate crystals and formation of coco-lycosomes, DCL. Group II received daily one capsule of 7 mg GA Lycopene formulated with medium saturated fatty acids, GAL-SMFA; group III—one capsule daily of 30 mg GAL-SMFA; IV group— one capsule daily 30 mg of GA lycopene formulated with polyunsaturated fatty acids, GAL-PUFA; V group—10 mg of the control dark chocolate daily.

Three GAL (GAL=formulated lycopene) groups received blinded lycopene capsules, as two other groups received blinded DC (dark chocolate) products.

Inclusion Criteria were:
 ability to sign an informed consent,
 light-to-moderate smokers (10 cigarettes daily),
 moderately obese with BMI between 30 and 35 kg/m2,
 with elevated serum markers of inflammatory oxidative damage, IOD≥40 μM/mL and oxidative stress, LDL-Px, ELISA×$10^3$≥200,
 no participation in other dietary trials during the last 3 months before enrolment and duration of study,
 willingness and ability to comply with the study protocol for the duration of the study.

Exclusion Criteria were:
 unwillingness to sign informed consent,
 unable to comply with the protocol for the duration of the study,
 history of myocardial infarction in the 3 months preceding the study, ejection fraction (EF)<45%,
 significant medical condition that would impact safety considerations (e.g., significantly elevated LFT, hepatitis, severe dermatitis, uncontrolled diabetes, cancer, severe GI disease, fibromyalgia, renal failure, recent CVA (cerebrovascular accident), pancreatitis, respiratory diseases, epilepsy, etc.),
 compulsive alcohol abuse (>10 drinks weekly),
 or regular exposure to other substances of abuse,
 participation in other nutritional or pharmaceutical studies,
 resting heart rate of >100 beats per minute or <50 beats per minute, positive test for tuberculosis, HIV, or hepatitis B,
 unable to tolerate phlebotomy,
 special diets in the 4 weeks prior to the study (e.g., liquid, protein, raw food diet),
 tomato intolerance.

Products. All products for the trial were developed and made by Lycotec Ltd. (Cambridge, United Kingdom). The product was especially designed to improve lycopene bioavailability in middle-aged persons, 50 years old or above, or in those who have such conditions as metabolic syndrome, fatty liver, etc. It contained phosphatidylcholine, which serves as principle scaffolding element for incorporation of lycopene during lipoprotein intracellular re-assembly, the process that is essential for lycopene transportation but impaired in the above individuals.

There were two formulations of GAL, for two different nutraceutical applications, were applied in this study. The first one was with a blend of SMFA to facilitate formation of small-medium chylomicrons, which would be transported by the portal vein for liver targeting delivery of lycopene. The second one was a blend with PUFA to facilitate formation of larger chylomicrons, which would be transported by the thoracic duct for the systemic blood circulation bypassing the liver. All GAL products were made in gelatin capsule.

For the control DC and DCL Green & Black's 70% dark chocolate was used. It was made from Trinitario cocoa beans and contained: 42% fat, of which saturates were 25%; carbohydrates 36.5%, of which sugars were 28.5%; fibre 10%, protein 9.1%, salt 0.13%. Each 10 g bar contained 1.5 mg of catechins, 6.6 mg of epicatechins, 1.9 mg of dimer-B2, 7.5 mg of caffeine, 75 mg of theobromine, 75 pg of phenylethylamine, 55 μg of serotonin, ≤0.1 pg of resveratrol. Both capsule and chocolate products were advised to be taken once a day after the main meal.

The period of administration was 1 month.

Methods.

BMI, Pulse Rate, and BP.

Measurements of body mass index, BMI, body mass of the patients and their height were carried out in the morning and BMI was calculated in kg/m2. Pulse rate, systolic and diastolic blood pressure, SBP and DBP, were recorded three times on the left arm of the seated patient after 15 min of rest. The time between measurements was greater than 2 minutes. The mean result for each parameter was calculated. All body and vascular parameters were recorded in the morning between 8 and 10 am.

Tissue Oxygenation. Thenar eminence and forearm muscles of the patients were used as a tissue target for the assessment of oxygen saturation, $StO_2$, or combined level of oxygenated haemoglobin and myoglobin. $StO_2$ was assessed by continuous wavelength near-infrared spectroscopy, NIRS, with wide-gap second-derivative (In Spectra, Hutchinson Technology, MN, USA). The measurements were taken at different time points. The recording was initiated after 15 min of rest in a supine position before occlusion of the brachial artery. It was then continued during stagnant ischemia induced by rapidly inflating the cuff to 50 mm Hg above systolic BP. The ischemia lasted for 3 min, and the recording period lasted for another 5 min after that until StO2 was stabilized. The area under the hyperaemic curve, AUC, of the recorded signal for the settling time in the post-occlusion period was then calculated as described earlier in % O2/minute [Costes F. et al, 1999, Marseglia L. et al, 2105].

Samples Collection. Blood was collected by phlebotomy in the morning, in the hospital, from the arm veins of patients following night fast. The serum was separated from the rest of the clotted mass by centrifugation, aliquots were then stored in code-labeled tubes for blinded analysis and stored at −80° C. until use.

For sample collection from the surface of the facial skin and samples of the cerumen all study participants were requested to avoid facial and ear hygienic manipulations for 24 hours before sampling, which was carried out in the morning in parallel with blood sample collection. Briefly, samples were collected using polyester swabs from the surface of the facial skin (the sides of the nose). During the procedure two samples were taken (one swab per side). Each collected sample was placed on the surface of a microscope slide. A second microscope slide was pressed against the surface of the first one. This procedure provided a pair of identical smears. All slides with collected samples were coded to provide sample anonymity for blinded analysis and stored at −20° C. until further analysis.

The stool samples were collected either in the morning or night before the day of the visit to the hospital. They did this collection themselves, at the convenience of their home. For this purpose participants used a special kit and sample containers which were provided by the trial team. The collected samples were labeled and stored at −80° C. until their analysis.

Gut Microbiome Analysis.

DNA Extraction

One ml of each fermentation endpoint (at 24 h) was pelleted via centrifugation at 13.000 g for 10 min and gDNA was extracted from the pellet using the Power Soil Kit protocol (MoBio Laboratories). The FastPrep bead-beating step was performed in 3 cycles of 15 s each at a speed of 6.5 M/s in a FastPrep-24™ Homogenizer (MP). DNA quantity and quality were measured using a NanoDrop 1000 (Thermo Scientific).

16S rRNA Gene Library Preparation

The fecal microbiota composition of in vitro fermentation samples were determined using tag-encoded 16S rRNA gene MiSeq-based (Illumina, CA, USA) high throughput sequencing. The V3 region of the 16S rRNA gene was amplified using primers compatible with the Nextera Index Kit (Illumina) NXt_338_F:5'-TCGTCGGCAGCGTCA-GATGTGTATAAGAGACAGACWCC-TACGGGWGGCAGCAG-3' (SEQ ID NO. 1) and NXt_518_R: 5'-GTCTCGTGGGCTCG-GAGATGTGTATAAGAGACAGAT-TACCGCGGCTGCTGG-3' (SEQ ID NO. 2) [OvreUs et al. 1997]. The PCR reactions and library preparation were conducted as described in [Kristensen et al. 2016].

High Throughput Sequencing and Data Treatment

The raw dataset containing pair-ended reads with corresponding quality scores were merged and trimmed using fastq_mergepairs and fastq_filter scripts implemented in the UPARSE pipeline. The minimum overlap length was set to 10 base pairs (bp). The minimum length of merged reads was 150 bp, the maximum expected error E was 2.0, and the first truncating position with quality score was N≤4. Purging the dataset from chimeric reads and constructing de novo Operational Taxonomic Units (OTU) were conducted using the UPARSE pipeline [Edgar 2013]. The Green Genes (13.8) 16S rRNA gene collection was used as a reference database [McDonald et al. 2012]. Quantitative Insight Into Microbial Ecology (QIIME) open source software [Caporaso et al. 2010] (1.7.0 and 1.8.0) was used for the subsequent analysis steps. Principal coordinate analysis (PCoA) plots were generated with the Jackknifed Beta Diversity workflow based on 10 UniFrac distance metrics calculated using 10 subsampled OTU tables. The number of sequences taken for each jackknife subset was set to 90% of the sequence number within the most indigent sample, hence xx000 reads per sample for the inulin and lactulose 16S rRNA library experiments and 87000 reads/sample for the HMO 16S rRNA library/experiments. Analysis of similarities (ANOSIM) was used to evaluate group differences using weighted and unweighted (Lozupone & Knight 2005) UniFrac distance metrics that were generated based on rarefied (xx000 reads/sample) OTU tables. The relative distribution of the genera registered was calculated for unified and summarized in genus level OTU tables. Alpha diversity measures expressed as observed species values (sequence similarity 97%) were computed for rarefied OTU tables (xx000 reads/sample) using the alpha rarefaction workflow. Differences in alpha diversity were determined using a t-test-based approach employing the non-parametric (Monte Carlo) method (999 permutations) implemented in the compare alpha diversity workflow. The ANOVA determined significance of quantitative (relative abundance) association of OTUs with given categories, p values were False Discovery Rate (FDR) corrected. These were calculated based on 1000 subsampled OTU-tables rarefied to an equal number of reads (xx000 reads/sample).

Biochemistry. Glucose, total cholesterol, triglycerides, high density cholesterol, low density cholesterol, C-reactive protein were determined using commercially available analytical kits according to the manufacturers' instructions (ByoSystems, R&D Systems).

Lycopene Quantitative Analysis. The lycopene concentration in all serum samples was measured in duplicate by high-performance liquid chromatography with modifications. Briefly, 400 μl of serum was mixed with 400 μl of ethanol and was extracted twice with 2 ml hexane. The combined hexane layers were evaporated to dryness in a vacuum (Scan Speed 32 centrifuge) and the residue reconstituted to a volume of 100 μl in sample solution (absolute ethanol-methylene chloride, 5:1, v/v). The specimens were centrifuged again (15 minutes at 10,000 g) and clear supernatant was transferred to HPLC vials. Five microliters of the extract was injected into an Acquity HSS T3 75×2.1 mm 1.8 μm column (Waters, USA) preceded by a Acquity HSS T3 1.8 μm VanGuard precolumn (Waters, USA) and eluted isocratically at 45° C. with the mobile phase (acetonitrile-0.08% phosphoric acid solution-tert-Butyl methyl ether, 70:5:25, v/v/v) at a flow rate of 0.5 ml/min. The lycopene peak was detected by a Photodiode Array Detector (Waters, USA) at 474 nm. The peak area was measured using Empower 3 software (Waters, MA). The lycopene concentration in serum samples was calculated by reference to an analytical standard (lycopene from tomato, L9879, Sigma, USA).

Inflammatory Oxidative Damage (IOD). Serum samples were incubated overnight in 0.05 M PBS acetate buffer (pH 5.6) to imitate the type of oxidative damage which occurs during the release of lysosomes following neutrophil degranulation. The following morning the reaction was stopped using trichloroacetic acid. The concentration of the end products such as malonic dialdehyde (MDA), and other possible thiobarbituric acid reactive substances (TBARS), was then measured by colorimetry using reagents and kits from Cayman Chemical (MC, USA).

LDL-Px and Lipoprotein 02. Activity of serum LDL peroxidase proteins, which include IgG with superoxide dismutase activity, was measured as described previously [Petyaev]. Plasma oxygen, which carried by blood lipids/lipoproteins was measured by catalymetry.

Statistics. For the assessment of normally distributed parameters the Shapiro-Wilk method was used. Student's t-test was then applied for both paired and unpaired samples. In cases where parameters were not normally distributed the Mann-Whitney test and Kruskal-Wallis test were used. ANOVA and ANCOVA were used with post hoc analysis (Statistica 9 suite, StatSoft; Inc.). Statistical significance between two-tailed parameters was considered to be P<0.05.

Results

General Characteristics of the Study Population

Baseline characteristics of the participants are presented in the table 1. Apart of their increased BMI all other measured parameters, from cardiovascular to blood biochemistry, were within the norm.

TABLE 1

BASELINE CHARACTERISTICS OF THE ENROLLED VOLUNTEERS
(Mean +/− SD)

|  | Groups | | | | |
| --- | --- | --- | --- | --- | --- |
|  | I | 11 | III | IV | V |
| Number of Patients | 6 | 6 | 6 | 6 | 6 |
| Males | 3 | 2 | 4 | 3 | 3 |
| Females | 3 | 4 | 2 | 3 | 3 |
| Age | 61.8 ± 5.9 | 56.2 ± 5.9 | 56.1 ± 5.8 | 52.1 ± 5.1 | 63.2 ± 6.1 |
| Light/Moderate Smokers | 1 | 1 | 1 | 1 | 1 |
| Body Mass Index in kg/m2 | 32.1 ± 2.4 | 32.7 ± 3.3 | 33.8 ± 3.5 | 31.1 ± 3.2 | 31.8 ± 2.9 |
| Fasting Glucose mmol/dL | 6.1 ± 0.42 | 6.0 ± 0.45 | 5.7 ± 0.49 | 5.4 ± 0.43 | 5.5 ± 0.56 |
| Total Cholesterol mg/dL | 185 ± 14.3 | 181 ± 15.2 | 175 +14.7 | 187 +16.2 | 180 +13.9 |
| Triglycerides mg/dl | 135 ± 14.9 | 136 ± 13.8 | 136 ± 13.8 | 127 ± 13.1 | 122 ± 13.5 |
| LDL mg/dL | 144 ± 11.8 | 143 ± 12.7 | 121 ± 12.2 | 137± 13.6 | 131 ± 12.1 |
| HDL mg/dL | 41.9 ± 3.2 | 46.5 ± 4.4 | 51.2 ± 4.7 | 49.8 ± 4.4 | 44.0 ± 4.4 |
| Pulse rate per min | 66.7 ± 4.2 | 67.7 ± 3.5 | 65.2 ± 3.4 | 70.5 ± 3.9 | 66.6 ± 5.1 |
| Blood Pressure |  |  |  |  |  |
| Systolic | 112 ± 5.5 | 123 ± 7.4 | 117 ± 6.9 | 124 ± 8.5 | 118 ± 6.7 |
| Diastolic | 77.6 ± 4.4 | 78.7 ± 5.0 | 77.6 ± 4.4 | 76.7 ± 4.6 | 79 ± 5.6 |

Gut Microbiome

Results of changes in the gut microbiome after one month of supplementation with 20 mg of formulated lycopene are presented in FIG. 1 and FIG. 2.

After 4 weeks of supplementation with GA lycopene, we have detected a shift in the gut microbial communities of the intervention participants. The relative abundance of Phyla level changed with a trend to increased relative abundance in Actinobacteria in all intervention groups, Group IV 4.5%-7.12% (p=0.51), Group III with 1.12% 3.22% p=0.04 (FDR corr), Group II, 2.52% 2.85%, p=0.8).

Members of the Phyla Bacteroidetes decreased in the relative abundance in all groups even though not statistically significant, Group IV 4.92%-2.72%, p=0.52; Group III 12.4% to 7.2%, p=0.8 FDR, Group2 31.26% to 21.05%, p=0.43.

Proteobacteria decreased in group IV (Group IV 1.7%-0.15%, p=0.28), whereas they increased in group III 0.9 to 10%, FDR p=0.5) in Group II the relative abundance of Proteobacteria remained the same with 0.95% and 0.92%, p=0.95.

The Phyla composition of the Gut Microbiota from intervention groups is shown in FIG. 1.

An increased Dose of Lycopene 30 mg Group III and IV vs Group II, 7 mg, was also reflected in an increased relative abundance of Actinobacteria (+2.6 Group IV, Group III+ 2.1%, Group II+0.33%).

Relative abundances at week 0 and week 4 at species level OTU are shown in Table 1.

When looking at the OTUs representative of the Bacteroidetes phyla it becomes clear that several Bacteroidetes species have decreased in relative abundance during GAL intervention across all GAL intervention groups (Group II, III, IV), but the effect was OTU specific as some members of the Bacteroidetes have also increased.

The OTU belonging to the family of Prevotellaceae, as well as the OTU *Prevotella stercorea, Prevotella, Bacteroides caccae, Prevotella copri*, Bacteroidetes—*Bacteroides ovatus*, an OUT of Paraprevotella.

DC Group V dark chocolate decreased the relative abundance of Actinobacteria 4.4-3.4%, p=0.7), Bacteroidetes did not change in relative abundance 6.4%-6.3% (p=0.9), Proteobacteria 6.6-2.4%, p=0.5).

DC and Lycopene Group I: Actinobacteria also increased (1.89% to 3.3%, p=0.2) after 4 weeks of intervention) Bacteroidetes on the other hand increased slightly from 23.4-25.8%, p=0.8), Firmicutes decreased (71.7-67.8%, p=0.8), Proteobacteria decreased from 0.49 to 0.24%, p=0.5 (Figure. 2).

When looking at Actinobacteria and the changes on the species OTU level, an increase of *Bifidobacterium longum* and *Bifidobacterium adolescentis* were observed and another *Bifidobacterium* species were observed across all GAL intervention.

On the Species OTU level Group I displayed a significant decrease in the OTU *Bacteroides* unassigned (0.075 to 0.018, p=0.3), *Bifidobacterium adolescentis* increased 10 fold 0.006-0.06%, p=0.1.

Looking at the members of the phyla Firmicutes, an increase in an *Streptococcus* OTU was detected across all intervention groups The main phyla abundance of which benefited from the lycopene ingestion, whether it was taken in a capsule form or in a chocolate matrix, was Actinobacteria, and in particular Bifidobacteria *adolescentis* which has probiotic beneficial health effects.

Blood and Tissue Parameters

Ingestion of lycopene products for one month, either in the capsule format or in the chocolate matrix, resulted in a significant increase of its concentration both in the serum and in the ear skin excretion (table 2).

TABLE 2

Changes in blood and tissue parameters after supplementation with GA lycopene for one month.

| Parameters before and after 4 weeks of the trial | Groups | | | | |
|---|---|---|---|---|---|
| | I | II | III | IV | V |
| Lycopene in serum, in ng/ml | | | | | |
| before | 110 ± 17 | 110 ± 12 | 210 ± 19 | 90 ± 8.4 | 120 ± 22 |
| after | 500 ± 52** | 310 ± 30** | 430 ± 30** | 190 ± 14* | 170 ± 27 |
| Lycopene in cerumen, in ng/g | | | | | |
| before | 53 ± 9.5 | 40 ± 5.5 | 70 ± 10.2 | 750 ± 93 | 14 ± 7.6 |
| after | 102 ± 12.4* | 100 ± 12.5* | 90 ± 11.5 | 2,500 ± 237** | 12 ± 5.5 |
| Triglycerides mg/dL | | | | | |
| before | 135 ± 14.9 | 155 ± 12.1 | 128 ± 9.7 | 126 ± 10.2 | 122 ± 13.5 |
| after | 133 ± 11.5 | 150 ± 11.3 | 110 ± 8.5* | 123 ± 10.1 | 118 ± 11.7 |
| LDL, in mg/dL | | | | | |
| before | 144 ± 12.5 | 143 ± 12.4 | 121 ± 10.5 | 137 ± 11.7 | 131 ± 12.1 |
| after | 139 ± 10.1* | 134 ± 11.2* | 104 ± 9.8* | 124 ± 10.3* | 129 ± 10.2 |
| HDL, in mg/dL | | | | | |
| before | 41.9 ± 2.9 | 46.5 ± 3.7 | 49.8 ± 3.9 | 50.1 ± 4.2 | 44.0 ± 2.2 |
| after | 42.2 ± 3.1 | 47.8 ± 3.9 | 50.0 ± 4.6 | 51.2 ± 4.4 | 45.1 ± 2.4 |
| IOD, in pM MDA | | | | | |
| before | 142 ± 9.2 | 141 ± 12.7 | 115 ± 10.9 | 64 ± 5.8 | 177 ± 12.1 |
| after | 101 ± 8.7** | 92 ± 8.8** | 46 ± 4.5** | 42 ± 3.7* | 153 ± 11.9* |
| LDL-Px, in ELISA × $10^3$ | | | | | |
| before | 310 ± 29 | 550 ± 61 | 664 ± 63 | 420 ± 45 | 450 ± 41 |
| after | 250 ± 24* | 350 ± 29** | 379 ± 34** | 130 ± 12** | 370 ± 32* |
| Lipoprotein $O_2$, in pM | | | | | |
| before | 4.07 ± 0.29 | 3.89 ± 0.35 | 3.86 ± 0.32 | 3.07 ± 0.29 | 3.67 ± 0.31 |
| after | 5.26 ± 0.33* | 4.64 ± 0.33* | 4.55 ± 0.39* | 3.44 ± 0.27 | 5.27 ± 0.39* |
| $StO_2$, in AUC mm | | | | | |
| before | 81 ± 6.4 | 66 ± 5.2 | 67 ± 5.1 | 59 ± 4.4 | 76 ± 5.5 |
| after | 88 ± 6.9* | 79 ± 6.1* | 83 ± 7.1* | 79 ± 6.3* | 76 ± 6.3 |

*$p < 0.05$,
**$p < 0.001$

Supplementation with GAL-MSFA resulted in a dose-depended significant reduction of markers of oxidative damage and inflammation. 7 mg of lycopene was able to reduce IOD and LDL-Px, by the end of the month, by 49 μM MDA and by 200 ELISA units, whilst 30 mg reduced these parameters by 69 and 285, accordingly. 30 mg of GAL-MSFA was 3 fold more effective to inhibit IOD than the same dose of lycopene but in the GAL-PUFA formulation. This may potentially indicate on the possible of the liver origin of this blood marker. Effect of two formulations of lycopene on LDL-Px was similar (table 2)

DC with or without lycopene had a similar effect on the inhibition of IOD as 7 mg of lycopene. Although both chocolate products were able to reduce LDL-Px, their effectiveness was below than of lycopene itself.

Administration of either formulation of GAL, or lycopene with DC complex, resulted by significant changes in the profile of fasting lipoproteins, which are assembled and produced by the liver. GAL-MSFA reduced in a dose-dependent manner both LDL concentration and triglycerides. This liver-targeting formulation of lycopene, in 30 mg dose, was able to reduce the first parameter by 17 mg/dL and the second by 18 mg/dL. Supplementation with GAL-PUFA resulted in LDL reduction by 13 mg/dL and triglycerides by only 3 mg/dL. Lycopene in the L-tug complex with dark chocolate was also able to reduce LDL, however, changes caused by the ingestion of the control DC were not significant (table 2). By the end of the trial there were no changes in the serum concentration of HDL, glucose and liver enzymes, ALT and AST (results are not presented).

There were noticeable improvements in the molecular oxygen metabolism in all groups. In groups supplemented with GAL-MSFA $O_2$ concentration and its transportation by blood lipoproteins was increase by 18-19%. In the group that received GAL-PUFA this increase was lower, by 12%. In the group, which received control DC the increase in the lipoprotein $O_2$ was the highest, by 44%. These changes in the plasma oxygen transportation translated to benefit for peripheral tissue oxygenation but not in the control DC group. Ingestion of all lycopene products in a significantly boost of tissue oxygenation in skeletal muscles. Administration of GAL-MSFA demonstrated a dose dependent effect in changes of this parameter. However, 30 mg of lycopene in GAL-PUFA formulation was 25% more effective than the same dose of lycopene but in the GAL-MSFA formulation (table 2).

Development of the metabolic syndrome and ageing are accompanied by ongoing, often at a subclinical level, processes of inflammatory and oxidative damage which may lead to changes in the liver metabolism, vascular functions, increase body mass and development subclinical systemic tissue hypoxia. In our study we observed that supplementation with lycopene, especially formulated for effective bioavailability in middle-aged people, had antioxidant, anti-inflammatory and lipid-lowering effects which are in accordance with earlier reports [Petyaev, 2012]. These changed in the blood markers were accompanied, or maybe resulted, in the improvement in the peripheral tissue $StO_2$. The main contributor into this parameter is the skeletal muscle respiration, although skin oxygenation is part of it too.

There are a number of molecules within the food, which are not fully digestible; hence they can reach the colon and its microbiota. Carotenoids and lycopene in particular belong to these types of partially digestible molecules. In our study we observed that regular intake by moderately obese middle-aged persons of 7 or 30 mg of GA lycopene, whether in a capsule form or in a dark chocolate matrix, for one month resulted in a significant change in the profile of the gut microbiota, and in particular in the increase of the population of Bifidobacteria *adolescentis*. Bifidobacteria probiotics is one of the best known probiotics, which has a broad range of health beneficial properties not only in the gut environment but in the whole body too. This involves their ability to control bacterial and viral pathogens, stimulate local intestinal and systemic immune system, improve lipid metabolism and weight management [Servin, 2004 and Amy O'Callaghan]. The loss of the Bifidobacteria could be a significant factor associated with ageing [Arboleya, 2016]. Therefore, the observed changes in the inflammatory markers, blood lipids and age-associated changes in the tissue oxygenation and other parameters may not only be the result of lycopene accumulation in the body but may also be a result of the restoration of the population of Bifidobacteria *adolescentis* in the gut.

It was interesting that observed lycopene effects on the gut bacteria, blood markers of inflammation and oxidation, lipids produced by the liver and by the skin (sebum) and peripheral tissue oxygenation were all dose-dependent. This indicates either on the possible direct and parallel involvement of lycopene in affecting such different targets in the body independently, or there is "a bridge", signaling and/or metabolic, which closely interconnect the gut bacteria, and in particular Bifidobacteria *adolescentis* population, with the blood, liver and other tissues, which lycopene can control.

Whether lycopene molecules directly affected growth of the Bifidobacteria *adolescentis* or it was their indirect effect via systemic changes in subclinical inflammation and oxygenation of the tissues in the body, including its intestine and the colon. The improvement of metabolism and physiology of the gut tissues may lead to its better control of the microbiota and boost growth of health beneficial bacteria.

Whatever the nature of the prebiotic effect of lycopene, direct or indirect, this is, to the best of our knowledge, the first report that ingestion of a carotenoid has this new property. It is also, to the best of our knowledge, the first study to demonstrate that dark chocolate has a similar affect, albeit with a different probiotic target.

To conclude, the observed systemic effect of lycopene supplementation which includes improvement of gut, blood, liver lipid metabolism could be not just due to the carotenoid and dark chocolate properties themselves but also to their ability to be effective prebiotics for the Bifidobacteria.

REFERENCES

Costes F, Denis C, Roche F, Prieur F, Enjolras F, Barthelemy J C. "Age-associated alteration of muscle oxygenation measured by near infrared spectroscopy during exercise." *Arch Physiol Biochem.* (1999) April; 107(2):159-67.

Lucia Marseglia, Sara Manti, Gabriella D'Angelo, Antonio Nicotera, Eleonora Parisi, Gabriella Di Rosa, Eloisa Gitto and Teresa Arrigo "Oxidative Stress in Obesity: A Critical Component in Human Diseases" *Int. J. Mol. Sci.* (2015) 16, 378-400.

OvreUs L, Forney L, Daae F L, and Torsvik V. "Distribution of bacterioplankton in meromictic Lake Saelenvannet, as determined by denaturing gradient gel electrophoresis of PCR-amplified gene fragments coding for 16S rRNA." Applied and environmental microbiology (1997) 63:3367-3373.

Kristensen K H S, Wiese M, Rytter M J H, Özçam M, Hansen L H, Namusoke H, Friis H, and Nielsen D S. "Gut microbiota in children hospitalized with oedematous and non-oedematous severe acute malnutrition in Uganda." PLoS Negl Trop Dis (2016) 10:e0004369.

Edgar R C. "UPARSE: highly accurate OTU sequences from microbial amplicon reads." Nature methods (2013) 10:996-998.

Caporaso J G, Kuczynski J, Stombaugh J, Bittinger K, Bushman F D, Costello E K, Fierer N, Pena A G, Goodrich J K, and Gordon J I. "QIIME allows analysis of high-throughput community sequencing data." Nature methods (2010) 7:335-336.

McDonald D, Price M N, Goodrich J, Nawrocki E P, DeSantis T Z, Probst A, Andersen G L, Knight R, and Hugenholtz P. An improved Greengenes taxonomy with explicit ranks for ecological and evolutionary analyses of bacteria and archaea." The ISME Journal (2012) 6:610-618.

Petyaev I. M., Mitchinson M. J., Hunt J. V., Coussons P. J. "Superoxide dismutase activity of antibodies purified from the human arteries and atherosclerotic lesions." Biochem. Soc. Trans. (1998) v.26, S43-45.

Ivan M. Petyaev, Pavel Y. Dovgalevsky, Victor A. Klochkov, Natalya E. Chalyk, and Nigel Kyle "Clinical Study: Whey Protein Lycosome Formulation Improves Vascular Functions and Plasma Lipids with Reduction of Markers of Inflammation and Oxidative Stress in Prehypertension." The Scientific World Journal" (2012) article ID 269476, doi:10.1100

Servin A L. "Antagonistic activities of lactobacilli and bifidobacteria against microbial pathogens." FEMS Microbiol Rev. (2004) October; 28(4):405-440.

Amy O'Callaghan and Douwe van Sinderen "Bifidobacteria and Their Role as Members of the Human Gut Microbiota" Front Microbiol (2016) v. 7, doi: 10.3389/fmicb.2016.00925.

Arboleya S, Watkins C, Stanton C, Ross R P. "Gut Bifidobacteria Populations in Human Health and Aging." Front Microbiol (2016) 19, 7, 1204. doi: 10.3389/fmicb.2016.01204.

The invention claimed is:

1. A method for promoting growth or increasing the abundance of a *Bifidobacterium* in the gastro-intestinal tract, skin, mouth or urogenital system of a subject comprising administering to the subject a composition comprising a therapeutically effective amount of a carotenoid compound selected from the group consisting of lycopene, lutein, zeaxanthin, meso-zeaxanthin, astaxanthin, cryptoxanthins, flavoxanthin, and neoxanthin.

2. The method according to claim 1, wherein the carotenoid compound is a lycopene.

3. The method according to claim 1, wherein the *Bifidobacterium* is selected from the group consisting of *Bifidobacterium adolescentis*, *Bifidobacterium catenulatum*, *Bifidobacterium breve*, *Bifidobacterium infantis*, *Bifidobacterium bifidum*, *Bifidobacterium animalis*, *Bifidobacterium longum*, *Bifidobacterium lactis*, *Bifidobacterium pseudocatenulatum*, *Bifidobacterium longum*, *Bifidobacterium angulatum*, *Bifidobacterium kashiwanohense*, *Bifidobacterium dentum* or *Bifidobacterium stercoris*.

4. The method according to claim 1, wherein the subject is a human, a terrestrial animal or a sea animal.

5. The method according to claim 1, where carotenoid compound is an ingredient of a medical or functional food, or functional beverage, or in the form of a nutraceutical or pharmaceutical product.

* * * * *

SEQUENCE LISTING

<160> NUMBER OF SEQ ID NOS: 2

<210> SEQ ID NO 1
<211> LENGTH: 53
<212> TYPE: DNA
<213> ORGANISM: Artificial Sequence
<220> FEATURE:
<223> OTHER INFORMATION: Primer Sequence
<220> FEATURE:
<221> NAME/KEY: misc_feature
<222> LOCATION: (36)..(36)
<223> OTHER INFORMATION: W is A or T/U
<220> FEATURE:

```
<221> NAME/KEY: misc_feature
<222> LOCATION: (45)..(45)
<223> OTHER INFORMATION: W is A or T/U

<400> SEQUENCE: 1
tcgtcggcag cgtcagatgt gtataagaga cagacwccta cgggwggcag cag         53

<210> SEQ ID NO 2
<211> LENGTH: 51
<212> TYPE: DNA
<213> ORGANISM: Artificial Sequence
<220> FEATURE:
<223> OTHER INFORMATION: Primer Sequence

<400> SEQUENCE: 2
gtctcgtggg ctcggagatg tgtataagag acagattacc gcggctgctg g           51
```